US012797547B2

(12) United States Patent
Carlsson

(10) Patent No.: US 12,797,547 B2
(45) Date of Patent: Nov. 17, 2026

(54) MEDICAMENT DELIVERY DEVICE WITH TRANSPORT LOCK

(71) Applicant: SHL Medical AG, Zug (CH)

(72) Inventor: Daniel Carlsson, Nacka Strand (SE)

(73) Assignee: SHL Medical AG, Zug (CH)

( * ) Notice: Subject to any disclaimer, the term of this patent is extended or adjusted under 35 U.S.C. 154(b) by 356 days.

(21) Appl. No.: 18/704,294

(22) PCT Filed: Oct. 12, 2022

(86) PCT No.: PCT/EP2022/078340
§ 371 (c)(1),
(2) Date: Apr. 24, 2024

(87) PCT Pub. No.: WO2023/072590
PCT Pub. Date: May 4, 2023

(65) Prior Publication Data

US 2026/0124395 A1 May 7, 2026

(30) Foreign Application Priority Data

Oct. 26, 2021 (EP) .................................... 21204816

(51) Int. Cl.
*A61M 5/20* (2006.01)
*A61M 5/31* (2006.01)

(52) U.S. Cl.
CPC ............ *A61M 5/2033* (2013.01); *A61M 5/20* (2013.01); *A61M 2005/2073* (2013.01); *A61M 2005/3142* (2013.01)

(58) Field of Classification Search
CPC .................. A61M 5/20; A61M 5/2033; A61M 2005/2073; A61M 2005/3142
See application file for complete search history.

(56) References Cited

U.S. PATENT DOCUMENTS

| | | | | |
|---|---|---|---|---|
| 2013/0060232 | A1 | 3/2013 | Adlon | |
| 2014/0207076 | A1 | 7/2014 | Grunhut | |
| 2014/0243751 | A1 * | 8/2014 | Brereton ............ | A61M 5/3204 604/197 |

FOREIGN PATENT DOCUMENTS

| | | | |
|---|---|---|---|
| EP | 2583706 | A1 | 4/2013 |
| WO | 2006052737 | A1 | 5/2006 |
| WO | 2014154491 | A | 10/2014 |

OTHER PUBLICATIONS

International Search Report and Written Opinion for corresponding PCT application No. PCT/EP2022/078340 dated Jan. 12, 2023.

* cited by examiner

*Primary Examiner* — Tasnim Mehjabin Ahmed
(74) *Attorney, Agent, or Firm* — McDonnell Boehnen Hulbert & Berghoff LLP

(57) ABSTRACT

The present disclosure provides a power pack for a medicament delivery device. The power pack includes a tubular body including a protrusion having a second contact surface, and including a release button having a flexible arm having a first contact surface. The first and second contact surfaces are angled with respect to a lateral axis of the tubular body, such that if the release button is pressed towards a proximal end of the tubular body before the power pack is assembled with a front assembly, the contact surfaces abut and cause a blocking of the release button from moving further towards the proximal end. The blocking includes a pressing of the flexible arm radially outwards towards an inside wall of the tubular body. A corresponding release button, a tubular body and a medicament delivery device are also provided.

7 Claims, 3 Drawing Sheets

MEDICAMENT DELIVERY DEVICE WITH TRANSPORT LOCK

CROSS-REFERENCE TO RELATED APPLICATIONS

The present application is a U.S. National Phase Application pursuant to 35 U.S.C. § 371 of International Application No. PCT/EP2022/078340 filed Oct. 12, 2022, which claims priority to European Patent Application No. 21204816.9 filed Oct. 26, 2021. The entire disclosure contents of these applications are herewith incorporated by reference into the present application.

TECHNICAL FIELD

The present disclosure relates to the field of medicament delivery devices. In particular, the present disclosure relates to a power pack for such a device having a transport lock.

BACKGROUND

Autoinjectors and other types of medicament delivery devices are designed to allow for a user (e.g. a patient) to perform self-administration of a dose of a particular medicament in a controlled way. After positioning the device at the site of the body where the injection is desired, the user activates the device by pushing a release button. Pushing the release button releases a pre-compressed power spring which, when released, in turn drives a plunger rod towards the proximal end of the autoinjector. The plunger rod comes into contact with a syringe in which the medicament to be delivered is stored, and the movement of the plunger rod forces the medicament out of the syringe and into the injection site. In some autoinjectors, the movement of the plunger rod is also responsible for first inserting the needle into the bodily tissue at the injection site.

Autoinjectors can be manufactured and delivered from the factory in multiple parts, or sub-assemblies, where the parts can then be finally assembled at a later stage as needed. For example, the release button, pre-compressed power spring and plunger rod may be delivered as part of a so-called power pack, while the needle and syringe may be delivered as part of a so-called front assembly. In this way, a same power pack may e.g. be combined with front assemblies having different types of syringes and/or containing different kinds of medicaments.

In order to prevent a user from activating the power pack before it has been assembled with the front assembly, the power pack can include some form of transport lock. One available solution includes the release button having a flexible arm which extends towards the proximal end of the power pack, and which, if the release button is pressed, abuts e.g. a protrusion located on a wall of a body of the power pack in which the release button is arranged. This may prevent the release button from being sufficiently pressed to activate the power pack, as the abutting of the flexible arm and the protrusion restricts the possible length of travel for the release button. At the same time, the front assembly may be provided with a corresponding prying arm which extends in a distal direction, and such that when the front assembly and the power pack are assembled, the prying arm comes into contact with the flexible arm of the power pack and bends the flexible arm radially inwards such that it no longer abuts the protrusion, and such that the release button can then be pushed fully to activate the power pack and the autoinjector.

However, if excessive force is applied on the release button before the power pack has been assembled with the front assembly, such a solution may not be sufficient to keep the release button from being accidentally pushed, resulting in an undesired premature activation of the power pack which can be both inconvenient and even dangerous to the user of the device.

SUMMARY

To at least partially solve the above identified problem with accidental and undesired activation of the power pack before final assembly of the medicament delivery device, the present disclosure provides an improved power pack, an improved release button, an improved body for the power pack, and an improved medicament delivery device, as defined in the accompanying independent claims. Various alternative embodiments are defined in the dependent claims.

According to a first aspect of the present disclosure, a power pack for a medicament delivery device is provided. The power pack includes a tubular body extending along a longitudinal axis from a proximal end to a distal end. The tubular body includes a protrusion which extends radially inwards from a section of an inside wall of the tubular body. The protrusion includes a second contact surface. The power pack further includes a release button at least partially arranged within the tubular body and movable in relation to the tubular body along the longitudinal axis. The release button includes a flexible arm extending towards the proximal end. An end of the flexible arm includes a first contact surface. The first contact surface and the second contact surface are both angled with respect to a lateral axis of the tubular body, such that if the release button is pressed towards the proximal end before the power pack is assembled with a front assembly of the medicament delivery device, the first contact surface and second contact surface abut and cause a blocking of the release button from moving further towards the proximal end, the blocking including a pressing (due to the angling of the contact surface) of the end of the flexible arm radially outwards towards the section of the inside wall of the tubular body. During assembly of the power pack with the front assembly, a surface of a distally extending prying arm of a (proximal) housing included in the front assembly abuts and slides along an outer surface of the flexible arm causing the flexible arm to bend radially inwards such that the blocking of the release button from moving further towards the proximal end is prevented. The bending of the flexible arm radially inwards may be towards the longitudinal axis.

The present disclosure of the power pack according to the first aspect improves upon existing technology in that the first and second contact surfaces are angled with respect to the lateral (or radial) axis of the tubular body, such that if a force is applied on the flexible arm in the proximal direction (by e.g. pressing or hitting on the release button), the force transferred to the protrusion will be focused at the area of the second contacting surface closer to the inside wall of the tubular body (i.e., at the “root” of the protrusion). In addition to minimizing stresses, this causes the end of the flexible arm being pressed radially outwards and secured towards e.g. the section of the inside wall of the body, instead of instead risking being bent radially inwards after the flexible arm slipping and being bent radially inwards, thereby causing an accidental and undesired activation of the power pack. As the abutting of the two contact surfaces still prevents further movement of the release button towards the proximal end, this provides an improved transport lock which is less sensitive to for example impact forces applied on the release button during e.g. transport or mishandling of the power pack. During assembly of the power pack with the front assembly, the flexible arm may however still be able to interact with the prying arm of the front assembly such that the transport lock is disabled after final assembly by preventing the blocking of the release button.

In one or more embodiments of the power pack, the first contact surface and the second contact surface may be angled with respect to the lateral axis of the tubular body such that the first contact surface faces away from the section of the inside wall of the tubular body and radially inwards towards the longitudinal axis, and such that the second contact surface faces towards the section of the inside wall of the tubular body and radially outwards away from the longitudinal axis.

In one or more embodiments of the power pack, the end of the flexible arm may include an additional angled surface. The additional angled surface may form part of the outer surface of the flexible arm. The additional angled surface may be angled with respect to the lateral axis of the tubular body such that the additional angled surface faces towards the section of the inside wall of the tubular body and radially outwards away from the longitudinal axis. During the assembly of the power pack with the front assembly, the surface of the prying arm abuts and slides along the additional angled surface to cause at least part of the bending of the flexible arm radially inwards.

In one or more embodiments of the power pack, the release button may have a tubular body extending along the longitudinal axis. The flexible arm may be formed as part of an outer shell of the tubular body of the release button.

In one or more embodiments of the power pack, the tubular body of the power pack may include an inner tubular section. The inner tubular section may be arranged fixed relative to the tubular body and extending along the longitudinal axis. The power pack may further include a power spring and a plunger rod. The power spring and the plunger rod may be coaxially arranged at least partly within the inner tubular section. The power spring may be compressed and abut a proximal rim of the plunger rod such that, when the power spring is released by the moving further of the release button towards the proximal end, the power spring may drive the plunger rod along the longitudinal axis towards the proximal end. In some embodiments, the power spring may be arranged on the outside of the plunger rod.

In one or more embodiments of the power pack, the inner tubular section may include a distal flexible arm. The distal flexible arm may be configured to abut a distal rim of the plunger rod to block the power spring from being released and (also block) the plunger rod from moving along the longitudinal axis towards the proximal end (due to e.g. the proximal force applied from the compressed power spring). The release button may include a protrusion. This protrusion may e.g. extend from a distal end of the release button and towards the proximal end of the tubular body. This protrusion may be configured to, as a result of the moving further of the release button towards the proximal end, abut a distal surface of the flexible arm of the inner tubular section and cause a bending of the flexible arm of the inner tubular section radially outwards, and thereby prevent the blocking of the power spring from being released and (the blocking of) the plunger rod from moving along the longitudinal axis towards the proximal end.

According to a second aspect of the present disclosure, a release button for a power pack for a medicament delivery device is provided. The release button extends along a longitudinal axis from a proximal end to a distal end. The release button is configured to be moveably arranged at least partially within a tubular body of the power pack (that is, moveably arranged with respect to the tubular body). The release button includes a flexible arm extending towards the proximal end. An end of the flexible arm includes a first contact surface. The first contact surface is configured to mechanically interact (e.g. abut) with a corresponding second contact surface of a protrusion of the tubular body to block a movement of the release button towards a proximal end of the tubular body. The first contact surface is angled with respect to a lateral axis of the release button, such that the first contact surface faces radially inwards and towards the longitudinal axis.

In one or more embodiments of the release button, an end of the flexible arm may include an additional angled surface forming part of an outer surface of the flexible arm. The additional angled surface may be angled with respect to the lateral axis of the release button such that the additional angled surface faces radially outwards away from the longitudinal axis.

In one or more embodiments of the release button, the release button may have a tubular body extending along the longitudinal axis. The flexible arm may be formed as part of an outer shell of the tubular body.

According to a third aspect of the present disclosure, a tubular body for a power pack for a medicament delivery device is provided. The tubular body extends along a longitudinal axis from a proximal end to a distal end. The tubular body is configured to receive a release button of the power pack such that the release button is movable (relative to the tubular body) along the longitudinal axis. The tubular body includes a protrusion which extends radially inwards from a section of an inside wall of the tubular body. The protrusion includes a second contact surface. The second contact surface is configured to mechanically interact (e.g. abut) with a corresponding first contact surface of a flexible arm of the release button to block a movement of the release button towards the proximal end along the longitudinal axis. The second contact surface is angled with respect to a lateral axis of the tubular body, such that the second contact surface faces radially outwards and away from the longitudinal axis.

According to a fourth aspect of the present disclosure, a medicament delivery device is also provided. The medicament delivery device includes a power pack according to the first aspect.

Other objects and advantages of the present disclosure will be apparent from the following detailed description, the drawings and the claims. Within the scope of the present disclosure, it is envisaged that all features and advantages described with reference to e.g. power pack of the first aspect are relevant for, apply to, and may be used in combination with also any feature and advantage described with reference to the tubular body of the second aspect, the release button of the third aspect, and the medicament delivery device of the fourth aspect, and vice versa.

BRIEF DESCRIPTION OF THE DRAWINGS

Exemplifying embodiments will now be described below with reference to the accompanying drawings, in which.

Figure 1A:
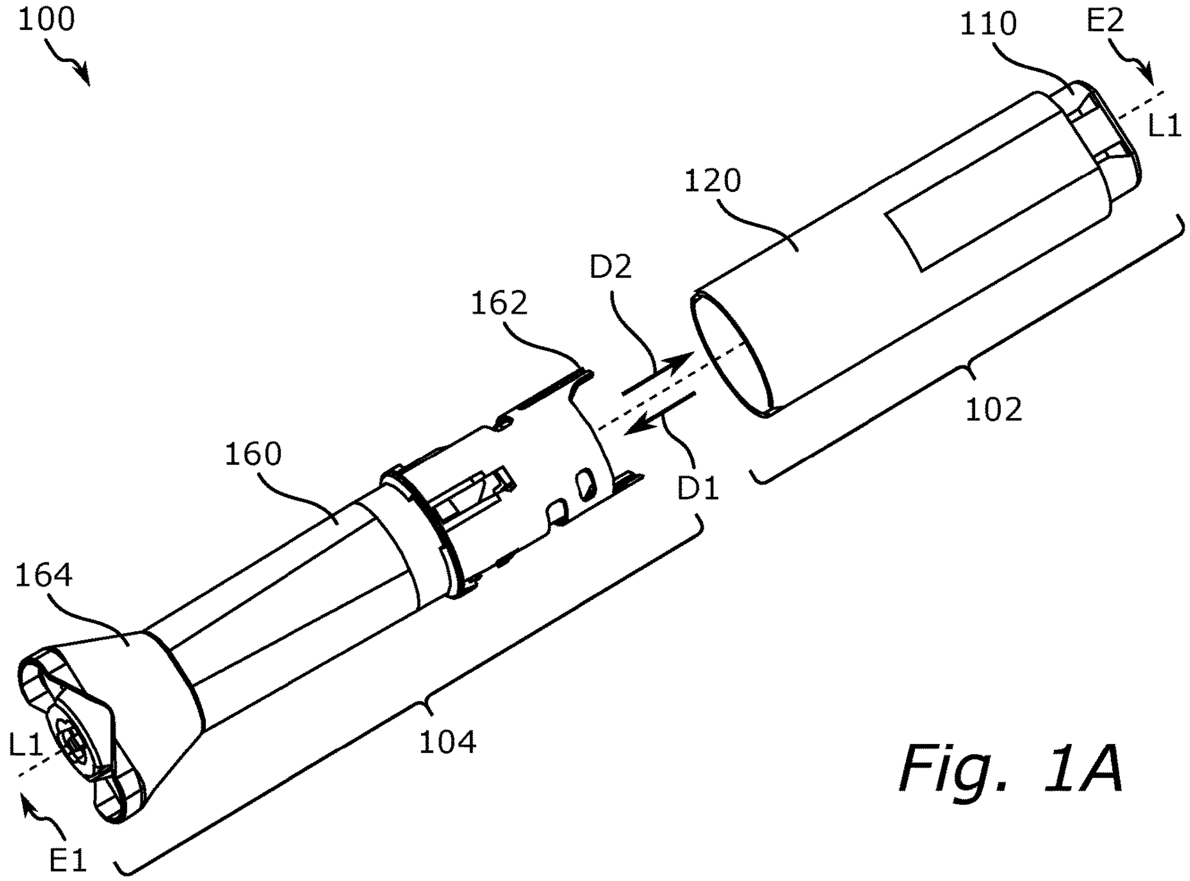
FIG. 1A schematically illustrates a perspective view of an embodiment of a medicament delivery device according to the present disclosure.

In the drawings, like reference numerals will be used for like elements unless stated otherwise. Unless explicitly stated to the contrary, the drawings show only such elements that are necessary to illustrate the example embodiments, while other elements, in the interest of clarity, may be omitted or merely suggested. As illustrated in the Figures, the (absolute or relative) sizes of elements and regions may be exaggerated or understated vis-à-vis their true values for illustrative purposes and, thus, are provided to illustrate the general structures of the embodiments.

DETAILED DESCRIPTION

Exemplifying embodiments of a medicament delivery device, a power pack, a tubular body, and a release button according to the present disclosure will now be described more fully hereinafter with reference to the accompanying drawings. The drawings show currently preferred embodiments, but the invention may, however, be embodied in many different forms and should not be construed as limited to the embodiments set forth herein; rather, these embodiments are provided for thoroughness and completeness, and fully convey the scope of the present disclosure to the skilled person.

FIG. 1A schematically illustrates a medicament delivery device 100 according to one embodiment of the present disclosure, wherein the device 100 is yet to be fully assembled. Hereinafter, the terms "medicament delivery device" and "device" will be used interchangeably.

The device 100 is manufactured as two sub-assemblies, namely a so-called power pack 102 and a so-called front assembly 104. The power pack 102 and the front assembly 104 are arranged such that they both extend along a longitudinal axis L1, from a proximal end E1 to a distal end E2. The power pack 102 includes a tubular body 120 and a release button 110, both extending along the longitudinal axis L1. The release button 110 is at least partially arranged within the tubular body 120 and is movable along the longitudinal axis L1. Here, "movable" implies that the release button can, if not blocked by any other component of the power pack, be pushed at least in a proximal direction D1 relative to the tubular body 120. Such pushing of the release button 110 can be achieved e.g. by a user using a finger, such as a thumb, to apply a force on the release button in the proximal direction.

Although not explicitly indicated in FIG. 1A, it is to be understood that each one of the power pack 102 and the front assembly can also be considered as having its own proximal and distal ends, and that each one of the power pack 102 and the front assembly 104 can also be considered as extending along its own longitudinal axis. When arranged as in FIG. 1A, the longitudinal axis of each sub-assembly aligns with the longitudinal axis L1 of the device as a whole. Likewise, the distal end of the power pack is also the distal end E2 of the device 100, while the proximal end of the power pack 102 is the proximal end E1 of the device 100. The proximal end of the power pack 102 can be understood as the end of the power pack 102 being closest to the front assembly 104 and, similarly, the distal end of the front assembly 104 can be understood as the end of the front assembly 104 being closest to the release button 110. Similarly, each particular component of the power pack 102 and the front assembly 104 can be defined as having its own proximal and distal ends, and also its own longitudinal axis. When so doing, it can be assumed that the components are all arranged as indicated in FIG. 1A. The references L1, E1 and E2 will be used throughout the present disclosure to indicate such longitudinal axis, proximal end distal ends of each component, as needed. Even if the device 10 is fully assembled, it is envisaged that the various proximal and distal ends of the various components are still as they where before the device 100 was fully assembled, as illustrated in FIG. 1A.

The front assembly 104 includes a (proximal) housing 160, where the housing 160 has a prying arm 162 extending in a distal direction D2. Here, "proximal" indicates that the housing 160 is a proximal part of the device 100 when assembled, but not necessarily a proximal part of the front assembly itself. The front assembly 104 can optionally also have a protective cap 164, which functions e.g. to protect a needle (not shown) of the front assembly 104 from being accessible by a user of the device 100. When the device 100 is to be used, after it has been fully assembled, the protective cap 164 can be removed by the user. In some embodiments, the device 100 can be configured (using e.g. a rotator, also not shown) such that even with the protective cap 164 removed, the device 100 must first be pressed against the injection site before the release button 110 can be used to activate the power pack and the device, and cause the injection of the medicament into the body of the user.

To fully assemble the device 100, the power pack 102 and the front assembly 104 can be pressed together such that e.g. the distal end of the front assembly 104 enters the proximal end of the tubular body 120 of the power pack 102. This will be elaborated on further below, when explaining the functioning of the various components of the power pack 102 and front assembly 104.

The various components of the device 100 as envisaged by the present disclosure will now be described in more detail with reference to FIGS. 1B-1F.

Figure 1B:
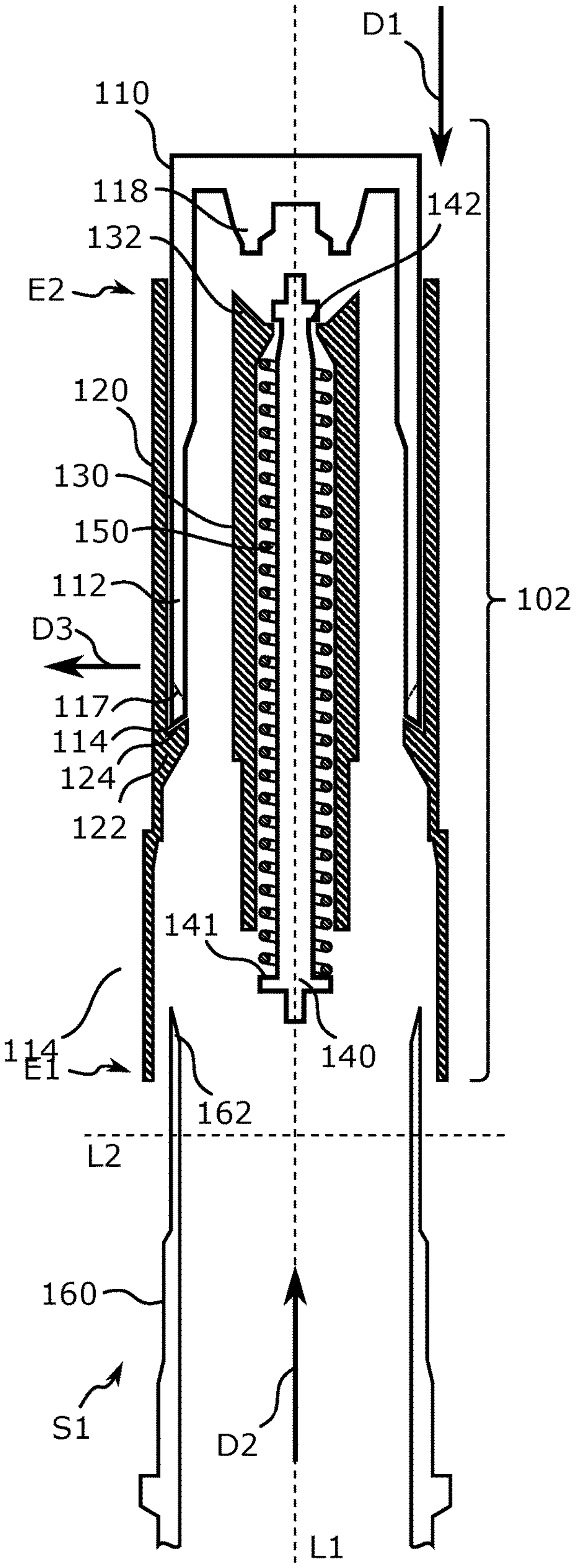
FIGS. 1B-1E schematically illustrate cross-sections of various embodiments of a power pack, a tubular body, and a release button according to the present disclosure, and FIG. 1F schematically illustrates a perspective view of an embodiment of a release button according to the present disclosure.

FIG. 1B schematically illustrates a cross-section of an embodiment of the power pack 102 and parts of the power assembly in a state S1 where the device is not yet assembled, i.e. when the power pack 102 and the front assembly has not yet been fully pressed together. The power pack 102 includes the release button 110 and the tubular body 120. The tubular body 120 extends along the longitudinal axis L1 from a proximal end E1 to a distal end E2. The tubular body 120 has a protrusion 122 which extends radially inwards from a section of an inside wall of the tubular body. Here, "radially inwards" is defined as pointing in a radial/lateral direction towards the longitudinal axis L1, while "radially outwards" is defined as pointing in a radial/lateral direction D3 away from the longitudinal axis L1. It is envisaged that the tubular body 120 may not necessarily be cylindrical, and that a "radial" direction is then a "lateral" direction instead. The protrusion 122 of the tubular body 120 has a second contact surface 124.

The release button 110 is at least partially arranged within the tubular body 120, and is movable (with respect to the tubular body 120) along the longitudinal direction L1 of the tubular body 120. The release button 110 has a flexible arm 112 which extends towards the proximal end E1 of the tubular body 120. The flexible arm 112 includes a first contact surface 114.

Because of the arrangement of the flexible arm 112 and the protrusion 122, in the state S1 of the device, the release button 110 can be pushed towards the proximal end E1 of the tubular body only until the first contact surface 114 of the flexible arm 112 abuts the second contact surface 124 of the protrusion 122. As a consequence, in the state S1 of the device, the first contact surface 114 and the second contact surface 124 causes a blocking of the release button from moving further towards the proximal end E1 than what is shown in FIG. 1B. By so doing, the release button 110 cannot be pushed sufficiently in the proximal direction D1 to cause an activation of the power pack 102.

Part of a mechanism of locking the power pack 102, a locking which may be removed by "activation" of the power pack 102, will be described in what follows. The tubular body 120 includes an inner tubular section 130 which is arranged within the tubular body 120 in a fixed manner, such that it cannot move with respect to the tubular body 120. Although not shown in the particular cross-section of FIG. 1B, the tubular body 120 may include e.g. on or more arms extending from its inside wall to the inner tubular section 130, in order to fixate the inner tubular section 130. The power pack 102 includes a power spring 150 and a plunger rod 140, which are both concentrically arranged at least partially within the inner tubular section 130. In the particular embodiment shown in FIG. 1B, the power spring 150 is arranged on the outside of the plunger rod 140. A distal end of the power spring 150 abuts e.g. part of the inner tubular section, while a proximal end of the power spring 150 abuts a proximal rim 141 of the plunger rod 140. In the state S1, the power spring is at least partially compressed and exerts a force on the plunger rod in the proximal direction D1 by the proximal end of the power spring 150 pressing against the proximal rim 141 of the plunger rod 140. To keep the plunger rod 140 from being propelled/driven by the power spring 150 in the proximal direction D1, a distal end of the inner tubular section 130 further includes a (distal) flexible arm 132. As shown in FIG. 1B, part of the flexible arm 132 abuts a corresponding distal rim 142 of the plunger rod 140, which blocks the plunger rod 140 from moving in the distal direction D2. As will be described in more detail later with reference to FIG. 1D, the holding/blocking of the plunger rod 140 caused by the flexible arm 132 and the distal rim 142 can be released by pressing of the release button 110 in the proximal direction D1.

In all the figures herein illustrating cross-sections, it should be noted that although some features are shown as being arranged in a same plane, that must not necessarily be the case. For example, in the power pack 102 illustrated in FIG. 1B, it may for example be envisaged that the features related to the activation/locking of the power pack 102, including e.g. the flexible arm 132 of the inner tubular section 130, are instead arranged in another plane, e.g. a plane perpendicular or otherwise angled with respect to the cross-sectional plane shown in FIG. 1B. However, for illustrative purposes only, the cross-sections shown are such that they illustrate all described features as lying in a same cross-sectional plane.

To further secure the release button 110 from being moved further in the distal direction D1 in the state S1, the envisaged power pack 102 is configured such that the first contact surface 114 and the second contact surface 124 are both angled with respect to a lateral axis L2 of the tubular body 120, as also shown in FIG. 1B. This angling of the contact surfaces prevents the first contact surface 114 from e.g. slipping radially inwards if excessive force is applied on the release button 110 in the proximal direction D1. If not prevented, such slipping of the first contact surface 114 radially inwards would e.g. risk causing a separation of the contact surfaces along the radial axis L2 such that the blocking of the release button 110 from moving further in the proximal direction D1 can no longer be provided. This, in turn, could lead to an accidental and undesired activation of the power pack 102, e.g. even before the device has been fully assembled. Such an accidental activation can for example be dangerous to the user, as the plunger rod 140, if accidentally propelled in the proximal direction D1 by the power spring, could e.g. hit the user or another person or object, and provide both pain and/or physical damage. In addition, if accidentally activated, the power pack may need to be replaced with a new power pack, leading to both an increased cost. This can be particularly inconvenient, and perhaps also dangerous, if the user is in a stressful situation where a proper use of the device as quickly as possible is desired.

By angling/tilting the first contact surface 114 and the second contact surface 124 as shown in FIG. 1B, a force applied on the release button 110 in the proximal direction D1 is instead transferred to the root of the protrusion 122, and causes, instead of a slipping of the first contact surface 114 radially inwards, a pressing of the end of the flexible arm 112 radially outwards towards (or even against) the section of the inside wall of the tubular body from which the protrusion 122 extends.

However, once the power pack 102 has been assembled with the front assembly of the device, it is desirable that the blocking of the release button due to the abutting contact surfaces 114 and 124 is removed, such that the device can then be used as intended. As envisaged herein, this is achieved by the proximal housing 160 of the front assembly having a flexible arm 162, a so-called "prying arm", which extends in a distal direction D2. The interaction of the front assembly and the power pack 102 during assembly of the device, when the front assembly is pressed and moved in the distal direction D2, will now be described in more detail with reference to FIG. 1C.

Figure 1C:
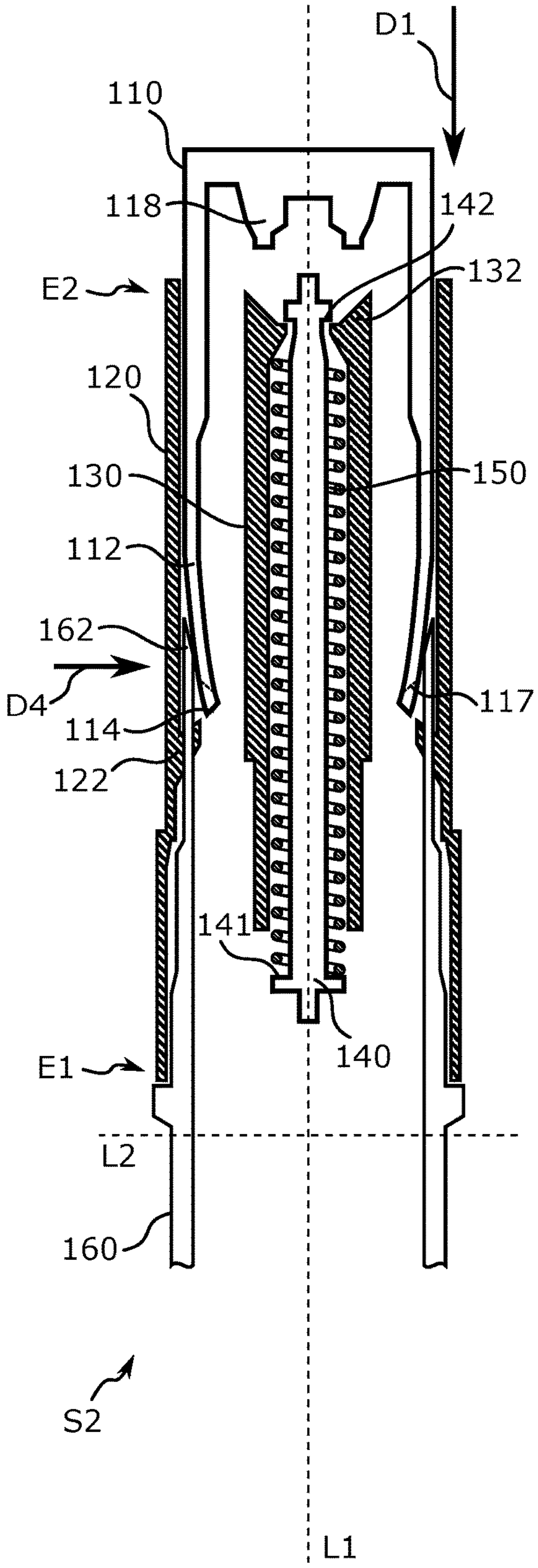

FIG. 1C schematically illustrates a cross-section of the same power pack 102 and front assembly as in FIG. 1B, but in another state S2 during assembly of the device in which the front assembly has been pushed towards the power pack 102 such that at least the prying arm 162 comes into contact with the flexible arm 112 of the release button 110. During the assembly, a surface of the distally extending prying arm 162 abuts and slides along an outer surface of the flexible arm 112, and causes the flexible arm 112 to bend radially inwards (in the radially inwards, lateral direction D4), as shown in FIG. 1C. This may also cause a slight movement of the release button 110 in the distal direction, and the bending of the flexible arm 112 can then cause a separation of the first contact surface 114 and the second contact surface 124 along the lateral axis L2 such that the blocking of the release button 110 from moving further towards the proximal end E1 of the tubular body 120 is prevented.

To further assist in the interaction between the prying arm 162 and the flexible arm 112 of the release button 110, as will be shown in more detail later with reference to FIG. 1F, the proximal end of the flexible arm 112 may, in some embodiments, optionally for example have an additional, angled surface 117 which forms part of the outer surface of the flexible arm, and which is angled opposite to the first contact surface 114. The prying arm 162 may for example be arranged and configured such that it interacts with the additional angled surface 117 of the flexible arm 112 but not with the first contact surface 114. During the assembly of the device, the surface of the prying arm 162 abuts and slides along the additional angled surface 117 and causes at least part of the bending of the flexible arm 112 radially inwards.

Once the flexible arm 112 has been bent radially inwards by the interaction with the prying arm 162 of the front assembly, the blocking of the release button 110 is removed and the release button 110 can then be further pressed/pushed to activate the power pack, as will now be described in more detail with reference to FIG. 1D.

Figure 1D:
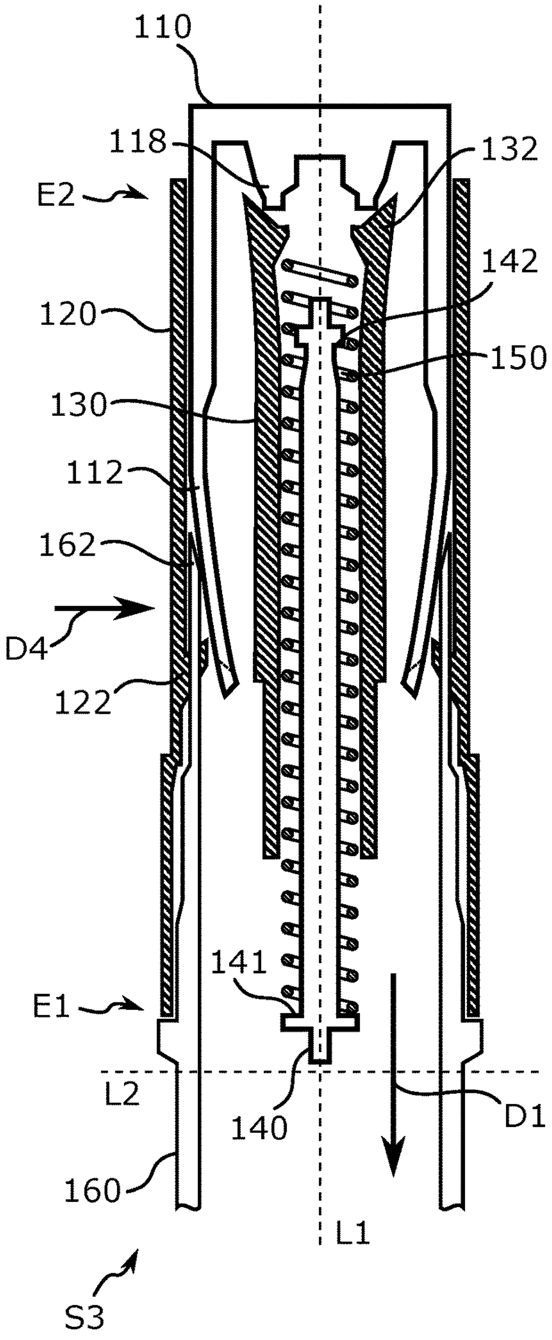

FIG. 1D schematically illustrates a cross-section of the same power pack 102 and front assembly as in FIGS. 1B and 1C, but in a state S3 wherein the blocking of the release button 110 has been removed, and where the release button 110 has been further pressed/pushed in the lateral direction D1 to cause an activation of the power pack 102. As the release button 110 is pushed, the flexible arm 112 is further bent radially inwards to allow for the release button 110 to move in the distal direction D1. At a distal end of an inside of the release button 110, there is provided a protrusion 118 which extends from a distal end of the release button towards the proximal end E1 of the tubular body 120. When the release button 110 is further pressed/pushed in the proximal direction D1, as shown in FIG. 1D, the protrusion 118 abuts a distal surface of the flexible arm 132 of the inner tubular section 130, and causes a bending of the flexible arm 132 radially outwards. When the flexible arm 132 is bent radially outwards, it is separated from the distal rim 142 of the plunger rod 140 and can no longer prevent/block the plunger rod 140 from being propelled/driven in the proximal direction D1 by the proximal force applied on the proximal rim 141 of the plunger rod 140 by the at least partially compressed power spring 150. As the power spring 150 expands, the plunger rod 140 is accelerated and moved along the longitudinal axis L1 in the proximal direction D1. This completes the activation of the power pack. The plunger rod 140 may then, in turn, reach and interact with e.g. a syringe/ampulla located in the front assembly, and cause an expulsion of a medicament from the syringe/ampulla. The movement of the plunger rod 140 may also, in some embodiments, be responsible for first causing a movement of a needle of the front assembly in the proximal direction, such that the needle is automatically inserted into the delivery site of the user before the medicament is expelled from the syringe/ampulla.

It should be noted that the features related to the activation of the power pack 102 (e.g. the inner tubular section 130, the flexible arm 132, the plunger rod 140, the rims 141 and 142, the power spring 150, etc.) and their interactions are here discussed for reasons of completeness, even though their exact function, arrangement and similar is not directly relevant to the core of the present disclosure, which is the angling of the first and second contact surfaces 114 and 124.

The angling of the contact surfaces 114 and 124, according to some embodiments of the present disclosure, will now be described in more detail with reference to FIG. 1E.

Figure 1E:
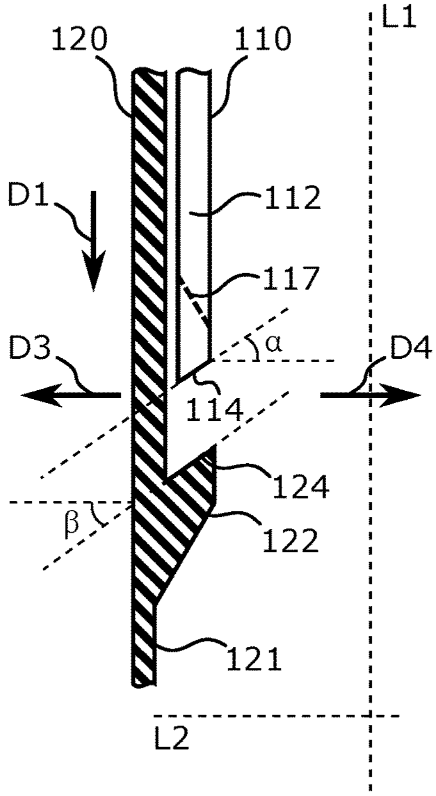

FIG. 1E schematically illustrates a cross-section of a part of the power pack, showing only the proximal end of the flexible arm 112 of the release button 110 and the corresponding part of the tubular body 120 where the protrusion 122 is provided. The first contact surface 114 is angled with respect to the lateral axis L2 of the tubular body 120 such that the first contact surface 114 faces away from the section of the inside wall 121 of the tubular body 120 (from which the protrusion 122 extends laterally/radially inwards) and towards the longitudinal axis L1. For example, this can be defined as any case where the angle α, formed between an extension of the plane of the first contact surface 114 and the lateral axis L2 as shown in FIG. 1E, is larger than zero but less than 90 degrees. The second contact surface 124 is angled with respect to the lateral axis L2 of the tubular body 120 such that the second contact surface 124 faces towards the section of the inside wall 121 of the tubular body 120, and radially outwards away from the longitudinal axis L1. For example, this can be defined as any case where the angle β, formed between an extension of the plane of the second contact surface 124 and the lateral axis L2 as shown in FIG. 1E, is larger than zero but less than 90 degrees. It is envisaged that an increased angling (that is, making the angles α and β larger) can provide a larger pressing of the end of the flexible arm 112 towards the inside wall 121 (for a same applied force on the release button 110 in the proximal direction D1), but at the cost of requiring a larger movement of the release button 110 and the flexible arm 112 in the distal direction when assembling the power pack with the front assembly, before the flexible arm 112 of the release button 110 can be bent radially inwards by the interaction with the prying arm of the front assembly. Likewise, making the angles smaller can require less movement of the flexible arm 112 in the distal direction before bending, but can provide a lower pressing of the flexible arm 112 towards the inside wall 121 (for a same applied force on the release button 110 in the proximal direction D1).

It is envisaged that in some embodiments, the contact surfaces 114 and 124 are not necessarily flat. However, the illustration in and discussion related to FIG. 1E can then still apply if the term "extension surface" is (re-)defined as e.g. a hypothetical, flat extension surface having a surface normal equal to an average surface normal of the contact surface in question, or similar. In general, herein, being "angled" (when referring to e.g. the first and second contact surfaces 114 and 124) should be taken to mean the corresponding surface being shaped such that the effect of converting a force applied on the release button 110 in the proximal direction D1 into an at least partially pressing of the flexible arm 112 radially outwards towards (or in some cases even against) the section of the inside wall 121 of the tubular body 120 wherein the protrusion 122 is arranged.

As described earlier herein, such angling of the first and second contact surfaces 114 and 124 and resulting pressing of the flexible arm 112 radially outwards prevents the applied force on the release button 110 in the proximal direction from causing a slipping of the first contact surface 114 radially inwards, and thereby avoids an accidental and undesired separate of the two contact surfaces 114 and 124 along the lateral axis L2.

FIG. 1E also illustrates the optional provision of the additional angled surface 117 of the flexible arm 112. In embodiments where such an additional angled surface 117 is provided, it is envisaged that e.g. the surface 117 may be angled with respect to the lateral axis L2 of the tubular body 120 such that the surface 117, contrary to the surface 114, faces towards the section of the inside wall 121 of the tubular body 120 and radially outwards away from the longitudinal axis L1, and such that during assembly of the device, the surface of the prying arm of the front assembly may abut and slide along the additional angled surface 117 to assist in, and cause at least part of, the bending of the flexible arm 112 radially inwards.

An exemplary embodiment of a release button 110 according to the present disclosure will now be described in more detail with reference to FIG. 1F.

Figure 1F:
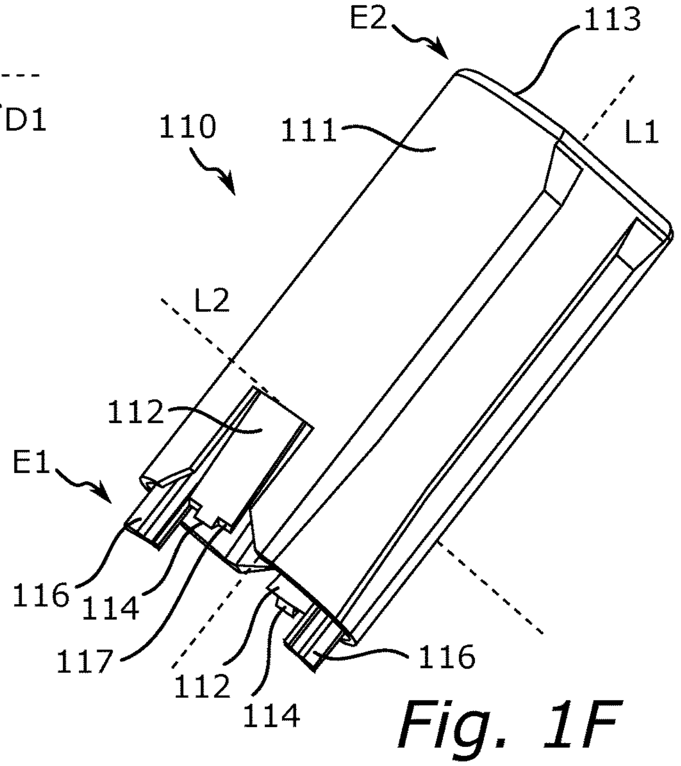

FIG. 1F schematically illustrates a release button 110. The release button 110 illustrated in FIG. 1F may for example correspond to or be equal to the release button 110 illustrated in any of FIGS. 1A-1E. The release button 110 has a tubular body 111 which extends along a longitudinal axis L1 from a proximal end E1 to a distal end E2. The release button includes a flexible arm 112, which extends towards the proximal end E1. The flexible arm 112 is formed as part of an outer shell of the tubular body 111. The tubular body 111 may for example be cylindrical, oval, or have any other suitable shape. Preferably, the shape of the tubular body 111 is configured to match the shape of the inside of the tubular body 120 of the power pack itself, in which the release button 110 is to be arranged movably, taking into account any deviations which may be needed to properly guide and hold the release button 110 within the tubular body of the power pack. The outer shape of the tubular body 111 of the release button 110 need not, for example, be completely circular, oval, etc., but may have deviations here and there including e.g. various guiding ribs, grooves, or similar, which may interact with corresponding features on the inside of the tubular body of the power pack.

In the example shown in FIG. 1F, the release button 110 includes two flexible arms 112, each having a first contact surface 114 which is angled as described earlier herein. In other embodiments, it is envisaged that the number of flexible arms may be different, and include e.g. only one flexible arm, or more than two flexible arms.

At the distal end E2 of the release button 110, there may for example be provided a pressing surface 113, against which the user may place e.g. a finger (such as a thumb) in order to push the release button 110 to activate the device. The release button 110 may also, in some embodiments, include various other structures, such as e.g. one or more protrusions 116 for interacting with the a rotator of the front assembly of the power pack, or similar, to provide other functionality of the device than the envisaged improved (transport) lock of the release button 110.

As also illustrated in FIG. 1F, it is envisaged that the flexible arm(s) may include, in some embodiments, the optional additional angled surface 117, which can assist in the bending of the flexible arm 112 by the prying arm of the front assembly, during assembly of the power pack and the front assembly. As shown in FIG. 1F, the additional angled surface is angled “oppositely” compared to the first contact surface 114, such that the first contact surface faces towards the longitudinal axis L1 while the additional angled surface 117 faces away from the longitudinal axis L1.

As described earlier herein, that a particular surface “faces towards” or “faces away from” an axis (or a surface/wall) does not require that e.g. a surface normal of the particular surface is exactly perpendicular to the axis. Instead, as long as the surface normal, or e.g. an average surface normal, or similar, of the particular surface has at least one component which is perpendicular to, and points towards, the axis in question, the particular surface is considered as facing towards that axis. Phrased differently, as long as e.g. an infinitely long vector starting at the particular surface and oriented in a same direction as a surface normal of the particular surface at some point intersects the axis, that particular surface is said to be facing towards the axis. Similarly, any particular surface that does not fulfill the above requirements are said to be “facing away” from the axis. The same reasoning applies also when saying that a particular surface faces away form/towards a particular other object such as a surface, or wall (such as e.g. the inside wall of the tubular body of the power pack, etc.).

In summary of FIGS. 1A-1F, it is concluded that the various components of the device 100, the power pack 102 and the front assembly 104 (such as the release button 110, the tubular body 120 and the prying arm 162 of the front assembly 104) as envisaged herein are configured to interact such that: i) in a state wherein the power pack and the front assembly are still to be assembled, the release button is blocked from being accidentally pushed (e.g. by external forces applied to the power pack) by the mechanical interaction between the protrusion and the flexible arm; ii) the blocking can be removed when the front assembly is finally assembled with the power pack (by bending the flexible arm using e.g. a prying arm of the front assembly), and iii) the angling of the contact surfaces of the flexible arm of the release button and of the protrusion of the tubular body, respectively, adds additional safety by improving the blocking by preventing accidental and undesired slipping of the flexible arm radially inwards. These features together provide a more flexible and improved device, power pack, release button and tubular body, wherein the power pack and front assembly can still be manufactured as separate sub-assemblies, but with an improved safety as accidental and undesired activation of the power pack (before assembly) can be further prevented.

Although not explicitly disclosed in any drawings, or at least not explicitly further described in the description so far, it is herein envisaged that the medicament delivery device may also include additional components, including e.g. the protective cap for the delivery members, an ampulla for storing the dose of medicament, one or more guiding rods and or other structures for the arrangement of the delivery member cover, a rotator for blocking pushing of the release button before e.g. the device is pressed against the injection site, etc. It is envisaged that any such components are not directly relevant for describing the idea behind the present disclosure, and any further illustration and/or discussion of such additional components has therefore, for reasons of clarity, been left out of the present disclosure.

Medicament delivery devices as envisaged herein may for example be autoinjectors containing insulin, allergy medicaments, epinephrine, migraine medicaments, atropine, or any other medicament/drug for which the use of a medicament delivery device as described herein is suitable. The device can e.g. be of a single-use type (i.e. disposable). Delivery members may include needles, parts of syringes, syrettes, or other suitable structures.

In the present disclosure, the term “longitudinal axis” of the device refers to an axis extending from a proximal end of the device to a distal end of the device, typically a central axis along the device in the direction of longest extension of the device. The term “distal end” refers to the part/end of the device, or the parts/ends of the members thereof, which under use of the device is/are located furthest away from the dose delivery/injection site. Correspondingly, the term “proximal end” refers to the part/end of the device, or the parts/ends of the members thereof, which under use of the device is/are located closest to the dose delivery/injection site. As described further above, this also apply to the various components of the device itself, such as the power pack, the front assembly, the release button, the tubular body of the power pack, etc., which can all be considered as having their own longitudinal axis (where applicable), and which, when assembled in the device, can all be considered as having also their own corresponding proximal and distal ends.

Although features and elements may be described above in particular combinations, each feature or element may be used alone without the other features and elements or in various combinations with or without other features and elements. Additionally, variations to the disclosed embodiments may be understood and effected by the skilled person in practicing the claimed invention, from a study of the drawings, the disclosure, and the appended claims.

In the claims, the words "comprising" and "including" does not exclude other elements, and the indefinite article "a" or "an" does not exclude a plurality. The mere fact that certain features are recited in mutually different dependent claims does not indicate that a combination of these features cannot be used to advantage.

The invention claimed is:

1. A power pack for a medicament delivery device, comprising:

a tubular body extending along a longitudinal axis from a proximal end to a distal end, wherein the tubular body comprises a protrusion which extends radially inwards from a section of an inside wall of the tubular body and includes a second contact surface; and a release button at least partially arranged within the tubular body and movable in relation to the tubular body along the longitudinal axis, wherein the release button comprises a flexible arm extending towards the proximal end and wherein an end of the flexible arm includes a first contact surface, wherein the first contact surface and the second contact surface are both angled with respect to a lateral axis of the tubular body, such that if the release button is pressed towards the proximal end before the power pack is assembled with a front assembly of the medicament delivery device, the first contact surface and second contact surface abut and cause a blocking of the release button from moving further towards the proximal end, the blocking including a pressing of the end of the flexible arm radially outwards towards the section of the inside wall of the tubular body, and wherein during assembly of the power pack with the front assembly, a surface of a distally extending prying arm of a housing comprised in the front assembly abuts and slides along an outer surface of the flexible arm causing the flexible arm to bend radially inwards such that said blocking of the release button from moving further towards the proximal end is prevented.

2. The power pack according to claim 1, wherein:

the first contact surface and the second contact surface are angled with respect to the lateral axis of the tubular body such that the first contact surface faces away from the section of the inside wall of the tubular body and radially inwards towards the longitudinal axis, and such that the second contact surface faces towards the section of the inside wall of the tubular body and radially outwards away from the longitudinal axis.

3. The power pack according to claim 2, wherein:

the end of the flexible arm includes an additional angled surface forming part of the outer surface of the flexible arm, the additional angled surface being angled with respect to the lateral axis of the tubular body such that the additional angled surface faces towards the section of the inside wall of the tubular body and radially outwards away from the longitudinal axis, and such that, during the assembly of the power pack with the front assembly, the surface of the prying arm abuts and slides along the additional angled surface to cause at least part of the bending of the flexible arm radially inwards.

4. The power pack according to claim 1, wherein:

the release button has a tubular body extending along the longitudinal axis, and the flexible arm is formed as part of an outer shell of the tubular body of the release button.

5. The power pack according to claim 1, wherein:

the tubular body of the power pack includes an inner tubular section arranged fixed relative to the tubular body and extending along the longitudinal axis, and wherein the power pack further comprises:

a power spring and a plunger rod coaxially arranged at least partly within the inner tubular section, wherein the power spring is compressed and abuts a proximal rim of the plunger rod such that, when the power spring is released by said moving further of the release button towards the proximal end, the power spring drives the plunger rod along the longitudinal axis towards the proximal end.

6. The power pack according to claim 5, wherein:

the inner tubular section includes a distal flexible arm configured to abut a distal rim of the plunger rod to block the power spring from being released and the plunger rod from moving along the longitudinal axis towards the proximal end, and the release button includes a protrusion extending from a distal end of the release button towards the proximal end of the tubular body, and configured to, as a result of said moving further of the release button towards the proximal end, abut a distal surface of the flexible arm of the inner tubular section and cause a bending of the flexible arm radially outwards, and thereby prevent the blocking of the power spring from being released and the plunger rod from moving along the longitudinal axis towards the proximal end.

7. A medicament delivery device, comprising:

a power pack according to claim 1.

* * * * *